United States Patent [19]

Roy et al.

[11] 4,166,019

[45] Aug. 28, 1979

[54] ELECTROCHEMICAL OXYGEN METER

[75] Inventors: Prodyot Roy, Saratoga; George J. Licina, Campbell, both of Calif.

[73] Assignee: General Electric Company, San Jose, Calif.

[21] Appl. No.: 784,412

[22] Filed: Apr. 4, 1977

Related U.S. Application Data

[63] Continuation-in-part of Ser. No. 616,940, Sep. 26, 1975, abandoned.

[51] Int. Cl.² .............................................. G01N 27/46
[52] U.S. Cl. ................................. 204/195 S; 204/1 T
[58] Field of Search .................................... 204/195 S

[56] References Cited
U.S. PATENT DOCUMENTS

| | | | |
|---|---|---|---|
| 3,297,551 | 1/1967 | Alcock | 204/1 S |
| 3,481,855 | 12/1969 | Kolodney et al. | 204/195 S |
| 3,576,730 | 4/1971 | Spacil | 204/195 S |
| 3,642,599 | 2/1972 | Franz | 204/195 S |
| 3,661,749 | 5/1972 | Richardson | 204/195 S |
| 3,719,574 | 3/1973 | Richardson | 204/195 S |
| 3,776,831 | 12/1973 | Roy et al. | 204/195 S |
| 3,794,569 | 2/1974 | Kawai et al. | 204/195 S |
| 3,864,231 | 2/1975 | Richardson | 204/195 S |
| 3,864,232 | 2/1975 | Handman et al. | 204/195 S |
| 3,883,408 | 5/1975 | Kim et al. | 204/195 S |
| 3,915,830 | 10/1975 | Isenberg | 204/195 S |
| 4,003,814 | 1/1977 | Tarassoff et al. | 204/195 S |

OTHER PUBLICATIONS

Patterson et al., "J. of the Electrochemical Soc.", vol. 114, No. 7, Jul., 1967, pp. 752-757.
Klinedinst et al., "J. Electrochem. Soc.", Sep., 1972, pp. 1261-1265.

*Primary Examiner*—T. Tung
*Attorney, Agent, or Firm*—Ivor J. James, Jr.; Sam E. Laub; Harold H. Green, Jr.

[57] ABSTRACT

An electrochemical device for measuring the concentration of oxygen in liquid alkali metal is described. Such device includes an elongated probe tube which is designed to be inserted into the liquid alkali metal whose oxygen content is of interest. A cup of a solid electrolyte material is bonded to the tube adjacent its lower end so that the outside surface of its bottom wall is in intimate contact with the liquid metal. The cup contains a mixture comprising a known concentration of one of the free metals gallium, indium and tin, and an oxide of such metal. This mixture is liquid at the temperature of operation of the device and is in intimate contact with the inner side of the bottom wall of the cup to provide a reference electrode. A high impedance volt meter is connected between the reference electrode provided by the mixture and the liquid alkali metal in order to provide a reading indicative of the EMF generated by ionic conduction of oxygen ions through the electrolyte and, hence, of the oxygen concentration in the alkali metal.

15 Claims, 1 Drawing Figure

U.S. Patent
Aug. 28, 1979
4,166,019
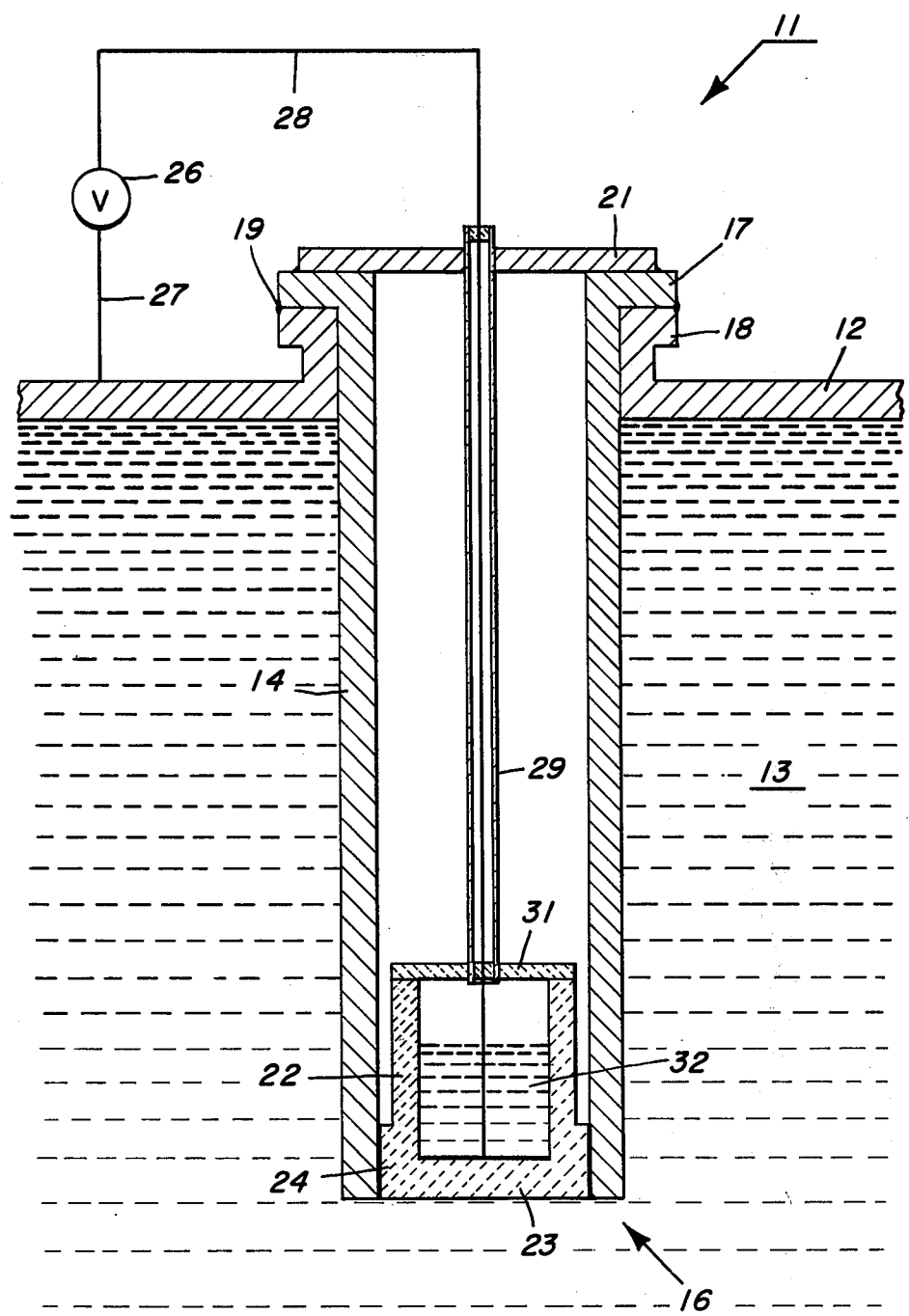

ELECTROCHEMICAL OXYGEN METER

REFERENCE TO RELATED APPLICATION

This is a continuation-in-part of U.S. patent application Ser. No. 616,940, filed Sept. 26, 1975, now abandoned.

BACKGROUND OF THE INVENTION

The present invention relates to an electrochemical device for measuring the concentration of oxygen in a liquid alkali metal and, more particularly, to such a device which has a longer life and is more reliable and accurate than prior devices of this nature especially designed to measure the concentration of oxygen in molten sodium.

It is desirable for various purposes to be able to measure the oxygen content of molten alkali metals used in industrial processes and commercial equipment. For example, it is quite important to be able to detect the presence of oxygen in the liquid sodium heat transfer loops of liquid metal fast breeder reactors. The presence of oxygen in the liquid sodium coolant of the primary coolant loop in such a reactor, i.e., the loop which passes through the reactor core, has to be minimized to prevent corrosion and consequent mass transport from the reactor core of radioactive corrosion products. A reliable oxygen monitoring device is also needed for the secondary loop of such a reactor liquid sodium coolant system in order to provide prompt and quantitative detection of steam or water leaks into the sodium.

Oxygen monitoring devices which rely on galvanic principles and ionic conduction have been designed to measure oxygen concentrations in molten metals. Basically, such devices provide an indication of the oxygen content by measuring the electromotive force generated between a reference electrode and a molten metal by the conduction of oxygen ions therebetween through a solid electrolyte. The devices described in U.S. Pat. Nos. 3,776,831; 3,864,231; and 3,864,232 are representative of such devices. Presently available electrochemical oxygen monitoring devices, however, suffer from several deficiencies which make them less than optimum for use in measuring the oxygen content in liquid alkali metals, especially if the alkali metal is, for example, liquid sodium being used as a fission reactor coolant.

One of the primary problems with most presently available devices is that they are not as accurate as desired. That is, most of such devices use air or some other gas as a reference electrode, and in order to provide a sufficiently fast response time the device must be operated at a relatively high temperature, e.g., 800° C. The difficulty with operation of such a device with a gas reference electrode at such a high temperature is that electronic conduction through the electrolyte becomes sufficiently high to interfere with the accurate measurement of ionic conduction through the solid electrolyte. Moreover, high temperature operation substantially increases corrosive action of the alkali metal on the solid electrolyte, thereby reducing the effective life of the device. While it may appear that such problems could be circumvented by operating at a lower temperature, for example, at temperatures around 550° C., such devices generally become irreversible with consequent potential drift during operation.

Also most presently available devices will not provide accurate readings when initially immersed in a liquid alkali metal having a concentration of oxygen in the range of parts per million. The electrolyte material used in such devices is generally comprised of a stoichiometric ceramic composition that has oxygen atoms removed when initially immersed in the alkali metal until an oxygen-depleted composition in equilibrium with the alkali metal is achieved. This removal of oxygen atoms from the electrolyte interferes with the accuracy of the operation of the device until an electrolyte with an oxygen depleted composition is achieved. Generally the kinetics of such removal of oxygen atoms from the electrolyte of the immersed device is very slow and a period of two or three months is required until the electrolyte material is in equilibrium with the alkali metal.

SUMMARY OF THE INVENTION

The present invention provides an electrochemical device for measuring oxygen activity in an alkali metal which circumvents the above problems. As a particularly salient feature of the instant invention, instead of the reference electrode being air or some other gas, it is a uniform mixture of a known concentration of one of the metals gallium, indium and tin, and an oxide of such metal, which mixture is liquid at the temperature of operation of the device and is in intimate contact with the solid electrolyte. Such a mixture has been found to be especially useful as the material for such a reference electrode because of its thermodynamic stability and lower melting temperature consistent with a desired lower temperature of operation of such a device. In order to eliminate the possibility of side reactions, the metal element selected for the mixture should also be the metal of the oxide.

The use of such a mixture as a reference electrode enables the oxygen monitoring device of the invention to operate both reversibly and accurately at temperatures within the range of between about 550° C. and 650° C. In this connection, the use of such a mixture as a reference electrode also eliminates electronic conduction interference with the desired measurement of ionic conduction of oxygen ions through the solid electrolyte.

Another salient feature of the device of the instant invention is a solid electrolyte which has been found to be compatible and stable (resistant to corrosive attack) at temperatures as high as 800° C. with both the preferred reference electrode mixtures and the alkali liquid metals, such as sodium, whose oxygen content typically is of interest. Basically, the material of the solid electrolyte consists of high purity thoria doped with yttria, which material is sintered and fired at a high temperature to obtain an actual density of 98% to 99% of its theoretical density.

In a particularly preferred embodiment of the device of this invention, a solid electrolyte is employed that has improved properties. The material of the solid electrolyte consists of high purity thoria doped with yttria, which material is sintered and fired for about two hours at a temperature of about 1650° C. and preferably at a temperature in the range of 1650° C. to 1700° C. in a reducing atmosphere of hydrogen containing about 1 to 2 percent by volume water vapor. This reducing heat treatment depletes the composition of the electrolyte of sufficient oxygen atoms to yield a stoichiometry that does not have removal of oxygen atoms when the electrolyte is initially immersed in an alkaline liquid metal having an oxygen content of about 1 to about 10 parts per million (ppm).

The meter of this invention is also mechanically designed to obviate those temperature variations in the electrolyte which cause many prior devices of this nature to be unreliable and shortlived. The mechanical design of the device further simplifies the manner in which such device is mountable to a vessel containing the high temperature liquid alkali metal whose oxygen content is to be monitored.

The invention includes other features and advantages which will be described or will become apparent from the following more detailed description of a preferred embodiment.

BRIEF DESCRIPTION OF THE DRAWING

With reference to the accompanying single sheet of drawing, FIG. 1 is a somewhat schematic and partial cross-sectional view of a preferred embodiment of the invention mounted within a molten metal flow pipe.

DETAILED DESCRIPTION OF THE PREFERRED EMBODIMENT

With reference to the drawing, a preferred embodiment of the electrochemical oxygen monitor of the invention is generally referred to by the reference number 11. Such device is shown extending through the wall 12 of piping containing the flow of a liquid alkali metal such as molten sodium 13. In this connection, the device 11 includes an elongated tube 14 of a non-corrosive metal which supports an electrochemical cell 16 within the sodium flow. The upper end of the probe tube 14, i.e., that end not in contact with the sodium, is provided with an outwardly projecting circumferential flange 17. Such flange mates with a corresponding flange 18 on the wall 12 circumscribing the piping aperture through which the probe tube 14 extends. Flanges 17 and 18 are suitably secured together, such as by a circumferential weld 19 as shown. Also, a top seal plate 21 closes the upper end of the tube 14 and seals its interior from the ambient atmosphere. Preferably, the interior of tube 14 is evacuated to, for example, $10^{-3}$ torr so that thermal expansion and contraction of a gas therewithin will not cause structural problems.

Electrochemical cell 16 is in the form of a cup 22 secured within the tube 14 adjacent its lower end so as to expose the exterior surface of its bottom wall 23 to intimate contact with the sodium 13. The cup 22 is secured within the tube 14 by a circumferential rim 24 circumscribing the lower end thereof and engaging the inner wall surface of the tube 14.

As will be discussed in more detail hereinafter, the material of the cup 22 and rim 24 is a yttria doped thoria (YDT), and such cup is preferably secured to the tube 14 with a fluid and gas tight seal formed by brazing. The tube 14 is preferably stainless steel or nickel in order to withstand the high temperature corrosive environment of liquid sodium, and a suitable brazing material between such a metal and the yttria doped thoria cup 22 is an intimate mixture of 70% by weight gallium and 30% by weight nickel. It is preferable that the cup 22 be fired at 1000° C. for one hour in a hydrogen atmosphere prior to the time the braze is formed. The outer surface of the circumferential rim 24 is then wetted with pure gallium before the cup is inserted into the end of the tube 14 and a braze paste of the gallium and nickel is applied thereto. The braze joint is formed by heating the joint so assembled to 1350° C. and maintaining the same at such temperature for three to five minutes under a vacuum of at least $10^{-6}$ torr. For best results, the braze joint is held at 800° C. for about one-half hour as it cools from the brazing temperature.

The bottom wall 23 of the cup 22 provides the oxygen ion conductive, solid electrolyte wall of the electrochemical cell. That is, its bottom or exterior surface is, as previously mentioned, in intimate contact with the molten sodium, whereas its opposite surface, the bottom interior surface of the cup, is in intimate contact with a reference electrode. The material of the cup is high purity thoria ($ThO_2$) doped with between about 7½% and about 15% by weight of yttria ($Y_2O_3$), preferably about 7½ to 8% by weight. The preferred range of 7½ to 8% by weight optimizes the electrical conductivity. Most desirably, the cup is sintered and fired at a high temperature in order to obtain an actual density which is at least about 98% of theoretical density. It has been found that such a high purity, dense yttria doped thoria electrolyte resists attack by molten sodium up to 800° C. Also, it has been found that such an electrolyte will provide essentially one hundred percent ionic conduction for oxygen ions at temperatures in the 550° C. to 650° C. range.

A particularly preferred process for making the cup involves mixing the $ThO_2$ and $Y_2O_3$ to achieve a homogeneous dispersion and forming a solid cup from the mixture by hot pressing at about 1900° C. at 4000 psi, thus achieving a sintered structure of at least about 98 percent of theoretical density. This process achieves a homogeneous dispersion (as determined by electron microprobe analysis) of $Y_2O_3$ in $ThO_2$ for optimum performance of the device. The solid cup is then machined to the shape of the cup 22. The machined cup is next subjected to a heat treatment to achieve a ceramic of a preferred stoichiometry namely an oxygen-depleted ceramic of about 85 to 92½ weight percent thoria with the balance being yttria. This is believed to yield, on a mole percent basis, the following structure: ($Th_{0.70}$ $to$ $0.85$, $Y_{0.30}$ $to$ $0.15)O_{2-x}$ where x is greater than 0.075, with x being greater than about 0.076 when Th is 85 mole percent and being greater than about 0.151 when Th is 70 mole percent. This heat treatment comprises firing the machined cup for about two hours at a temperature of about 1650° C. to about 1700° C. under a hydrogen atmosphere containing from about 1 to about 2 percent water vapor. The resulting ceramic is in equilibrium with liquid sodium containing from about 1 to about 10 ppm oxygen when immersed in the liquid sodium.

This heat treatment depletes the indicated amount of oxygen atoms from the electrolyte yielding a stoichiometry that does not involve the removal of oxygen atoms from the electrolyte when it is immersed in a liquid alkali metal. In theory this process is believed to yield a stoichiometry for the electrolyte having a Gibb's energy ($\Delta \bar{G}_{O_2}$/mole $O_2$) that is substantially equal to the Gibb's energy exhibited by the liquid alkali metal, particularly liquid sodium, containing from about 1 to about 10 ppm oxygen.

As a particularly salient feature of the instant invention, it includes a reference electrode which also provides essentially one hundred percent ionic conduction in the 550° C. to 650° C. range. Another feature of this invention is an electrolyte that is substantially isothermal during operation while immersed in the liquid/alkali metal due to the limited size of the cup. In its basic aspects, the reference electrode comprises a mixture of one of the metals gallium, indium and tin, and an oxide of such metal. While the mixture ratios must be known to allow calculation of the base oxygen activity in the reference electrode, the percentage of free metal to metal oxide is not crucial for operation of the reference electrode. There must be, however, sufficient free metal in the mixture for it to be in contact with the solid electrolyte wall 23 for the conduction of oxygen ions.

While from the theoretical standpoint a combination in the mixture of one of the above metals and any of its oxides will produce the desired results, there are certain metal/metal oxide mixtures which are especially suitable, particularly when it is the oxygen content of molten sodium which is of interest. That is, mixtures of tin (Sn) and stannic oxide ($SnO_2$); gallium (Ga) and gallium sesquioxide ($Ga_2O_3$); and indium (In) and indium sesquioxide ($In_2O_3$) are preferred. Both the free metal and the oxide of each of these mixtures is a relatively low viscosity liquid at the temperature of operation of the device (e.g., 550° to 650° C.) and have been found not to support electronic conduction interference with ionic conduction of oxygen ions through the electrolyte at such temperatures.

The operating principle of a galvanic cell including a liquid mixture of one of the above metals and its oxide as the reference electrode can be represented as follows:

| Oxygen in solution in sodium | YDT | Metal/metal oxide reference electrode |

The difference in oxygen activity across the electrolyte causes the ionic transport of oxygen through the YDT (yttria doped thoria) with a potential produced between the reference and sodium sides of the cell. The value of the open circuit potential is thus a direct measure of the activity of oxygen in the sodium.

For the regime in which ionic conductivity in the electrolyte predominates ($t_{ion} > 0.99$), the EMF of the cell is mathematically given by:

$$EMF = RT/4F \log_e P_{O_2}Na/P_{O_2} \text{ref}$$

where
F = Faraday Constant
R = Gas Constant
T — Temperature, °K.
$P_{O_2}$ = Oxygen Partial Pressure By fixing the oxygen activity of the reference electrode and closely monitoring cell temperature, the oxygen activity in sodium may be directly measured.

To obtain a measurement of such electromotive force, a high impedance (e.g., 10 megohm) volt meter which will draw insufficient current to affect the readings, is connected between the liquid sodium and the reference electrode to measure the EMF. That is, a high impedance volt meter 26 has one of its terminals connected via a lead 27 to the wall 12 of the liquid sodium piping, which piping will be at the same potential as the liquid sodium therein. The other terminal of the volt meter is connected to a lead 28 of a refractory metal, such as tungsten or molybdenum, which passes through seal plate 21 and the interior of the probe tube 14 via an electrical feedthrough insulator tube 29. As illustrated, tube 29 passes through a lid 31 on the cup 22, and lead 28 extends therethrough into contact with the liquid metal/metal oxide reference electrode 32 therein. The purpose of the lid 31 is to prevent reference electrode vapors from escaping from the cup and forming a short circuit between the reference electrode 32 and the tube 14. In this connection, it should be noted that the tube 14 will be at the same electrical potential as the sodium 13.

In operation, it is desirable in order to reduce thermal shock that the tube 14 and electrolyte cup 16 be slowly heated to the temperature of the molten metal within which they are to be submerged, prior to the time of such submerging. Then with the partial pressure of oxygen in the reference electrode known, the oxygen concentration in the molten sodium can be accurately determined by measuring both the temperature of the molten sodium adjacent the device and the EMF generated by the cell. The equation set forth above can then be used to calculate the partial pressure of oxygen in the molten sodium. It should be noted that precalculated tables can be provided for an operator, setting forth the partial pressure of oxygen in the molten sodium, with the temperature and EMF as variables.

While the invention has been described in connection with a preferred embodiment thereof, it will be appreciated by those skilled in the art that various changes and modifications can be made without departing from its spirit and scope. It is, therefore, intended that the coverage afforded applicant by the following claims be interpreted to encompass all reasonable changes and modifications.

We claim:

1. An electrochemical device for measuring the concentration of oxygen in a liquid alkali metal comprising:
   (a) an elongated tube of a noncorrosive metal having brazed in its open end by a braze material consisting essentially of an intimate mixture of gallium and nickel
   (b) a container defining an enclosed limited volume having on one side of the container an oxygen ion conductive, solid electrolyte body wall having a pair of opposite side surfaces, a first one of which surfaces is substantially even with and fills the open end of said tube and is adapted for intimate contact with the liquid metal whose oxygen concentration is to be measured;
   (c) a mixture in the enclosed limited volume comprising a known concentration of one of the metals selected from the group consisting of gallium, indium and tin, and an oxide of said metal, which mixture is liquid at the temperature of operation of said device and is in intimate contact with the second one of said electrolyte body wall side surfaces provide a reference electrode; and
   (d) means for measuring any electromotive force generated between said reference electrode and said liquid metal by the conduction of oxygen ions through said solid electrolyte to provide a reading indicative of said oxygen concentration.

2. The electrochemical device of claim 1 for measuring the concentration of oxygen in a liquid metal in which the constituents of said reference electrode mixture are selected from the group consisting essentially of tin and stannic oxide, gallium and gallium sesquioxide, and indium and indium sesquioxide.

3. The electrochemical device of claim 2 for measuring the concentration of oxygen in a liquid metal in which said ion conductive, solid electrolyte body wall consists essentially of a uniform mixture of about 7½ to about 15 percent by weight yttria with the balance being thoria and said electrolyte body wall has an actual density of at least about 98 percent of theoretical density.

4. The electrochemical device of claim 1 for measuring the concentration of oxygen in a liquid metal in which said ion conductive, solid electrolyte body wall consists essentially of thoria doped with yttria.

5. The electrochemical device of claim 4 for measuring the concentration of oxygen in a liquid metal in which said ion conductive, solid electrolyte body wall consists essentially of thoria doped with between about 7½ and 8 percent by weight of yttria.

6. The electrochemical device of claim 5 for measuring the concentration of oxygen in a liquid metal in which said electrolyte body wall consists essentially of about 92½ percent by weight thoria and about 7½ percent by weight yttria and said electrolyte body wall has an actual density of at least about 98 percent of theoretical density.

7. The electrochemical device of claim 1 for measuring the concentration of oxygen in a liquid metal wherein said oxygen ion conductive, solid electrolyte body wall is part of a cup of the material of said electrolyte which contains said mixture providing said reference electrode, and said cup is supported within the elongated tube which extends into said liquid metal whose concentration of oxygen is to be measured.

8. The electrochemical device of claim 7 for measuring the concentration of oxygen in a liquid metal wherein said cup is positioned in said tube with its bottom wall being the surface exposed to contact with the liquid metal.

9. An electrochemical device for measuring the concentration of oxygen in a liquid alkali metal comprising:
(a) an elongated tube of a noncorrosive metal having brazed in its open end by a braze material consisting essentially of an intimate mixture of gallium and nickel
(b) a container defining an enclosed limited volume having on one side of the container an oxygen ion conductive, solid electrolyte body wall comprised of a composition of a homogeneous dispersion of yttria in thoria, having a pair of opposite side surfaces, a first one of which surfaces is substantially even with and fills the open end of said tube and is adapted for intimate contact with the liquid metal whose oxygen concentration is to be measured, said composition comprising said wall being depleted of sufficient oxygen atoms so that upon immersion in the liquid alkali metal there is substantially no removal of oxygen atoms from said wall;
(c) a mixture in the enclosed limited volume comprising a know concentration of one of the metals selected from the group consisting of gallium, indium and tin, and an oxide of said metal, which mixture is liquid at the temperature of operation of said device and is in intimate contact with the second one of said electrolyte body wall side surfaces to provide a reference electrode; and
(d) means for measuring any electromotive force generated between said reference electrode and said liquid metal by the conduction of oxygen ions through said solid electrolyte to provide a reading indicative of said oxygen concentration.

10. The electrochemical device of claim 9 for measuring the concentration of oxygen in a liquid metal in which the constituents of said reference electrode mixture are selected from the group consisting essentially of tin and stannic oxide, gallium and gallium sesquioxide, and indium and indium sesquioxide.

11. The electrochemical device of claim 10 for measuring the concentration of oxygen in a liquid metal in which said oxygen depleted ion conductive, solid electrolyte body wall consists essentially of a uniform mixture of about 7½ to about 15 percent by weight yttria with the balance being thoria and said electrolyte body wall has an actual density of at least about 98 percent of theoretical density.

12. The electrochemical device of claim 9 for measuring the concentration of oxygen in a liquid metal in which said oxygen depleted ion conductive, solid electrolyte body wall consists essentially of thoria doped with between about 7½ and 8 percent by weight of yttria.

13. The electrochemical device of claim 12 for measuring the concentration of oxygen in a liquid metal in which said oxygen depleted electrolyte body wall consists essentially of about 92½ percent by weight thoria and about 7½ percent by weight yttria and said electrolyte body wall has an actual density of at least about 98 percent of theoretical density.

14. The electrochemical device of claim 9 for measuring the concentration of oxygen in a liquid metal in which said oxygen ion conductive, solid electrolyte body wall is part of a cup of the material of said electrolyte which contains said mixture providing said reference electrode, and said cup is supported within the elongated tube which extends into said liquid metal whose concentration of oxygen is to be measured.

15. The electrochemical device of claim 14 for measuring the concentration of oxygen in a liquid metal wherein said cup is positioned in said tube with its bottom wall being the surface exposed to contact with the liquid metal.

* * * * *